(12) United States Patent
Jeffers et al.

(10) Patent No.: US 6,319,723 B1
(45) Date of Patent: Nov. 20, 2001

(54) PARTS PER TRILLION DETECTOR

(76) Inventors: Eldon L. Jeffers, 209 Garfield, LaPorte, TX (US) 77571; Edward M. Ejzak, P.O. Box 58177, Webster, TX (US) 77598

( * ) Notice: Subject to any disclaimer, the term of this patent is extended or adjusted under 35 U.S.C. 154(b) by 0 days.

(21) Appl. No.: 09/191,091

(22) Filed: Nov. 12, 1998

(51) Int. Cl.[7] .................................................... G01N 1/40
(52) U.S. Cl. ........................ 436/133; 436/146; 436/178; 422/82.02; 422/90
(58) Field of Search .................................. 422/82.02, 88, 422/90; 436/133, 146, 177, 178

(56) References Cited

U.S. PATENT DOCUMENTS

| | | | |
|---|---|---|---|
| 3,958,941 | * | 5/1976 | Regan . |
| 5,141,717 | * | 8/1992 | McRae ............................ 422/82.01 |
| 5,518,608 | * | 5/1996 | Chubachi ............................ 210/96.1 |
| 5,531,961 | * | 7/1996 | Wright et al. ........................... 422/80 |
| 5,531,965 | * | 7/1996 | Duve ...................................... 422/80 |
| 5,902,751 | * | 5/1999 | Godec et al. ......................... 436/146 |
| 5,932,791 | * | 8/1999 | Hambitzer et al. .................. 73/19.01 |

* cited by examiner

*Primary Examiner*—Jeffrey Snay
(74) *Attorney, Agent, or Firm*—The Matthews Firm; William P. Remey, III

(57) ABSTRACT

An apparatus is disclosed which is capable of detecting a selected gas in a liquid sample to a sensitivity in the range of 10 to 10,000 parts per trillion. Such sensitivity is achieved by concentrating the selected gas in a sample without concentrating sources of ionic interference that are also present in the sample. Selective concentration of the gas is achieved by vaporizing the sample, correcting for non-ideal vaporization, selectively condensing the selected gas from the vapor, and detecting the selected gas. Methods for using the apparatus and detecting the selected gas are also disclosed.

29 Claims, 5 Drawing Sheets

PARTS PER TRILLION DETECTOR

BACKGROUND

An apparatus is provided which is capable of detecting a selected gas in a sample with a sensitivity of less than one part per billion ($10^9$) parts; that is, with a sensitivity in the range of parts per trillion ($10^{12}$). Methods for detecting a selected gas in a sample with a sensitivity in the range of parts per trillion are also disclosed. The apparatus and methods provide for detection of a selected gas in amounts as low as 10 parts per trillion ($10^{12}$).

The apparatus and methods disclosed herein provide means whereby a selected gas in a relatively large sample volume is concentrated into a relatively small volume. Substantially all the gas is recovered from the sample and is concentrated in a small volume of water.

Ordinarily, concentration of a sample also results in concentration of salts and other contaminants in the sample. The presence of such salts and contaminants, that is, any component that is not the sample carrier, such as water, or the gas of interest, in the sample creates ionic interferences in the detection of a selected gas of interest in the sample, thereby reducing the sensitivity with which the selected gas can be detected.

The present apparatus and methods, however, concentrate the selected gas of interest but substantially eliminate the ionic interference one would otherwise expect from concentration of the sample. By obviating ionic interference, the present apparatus and methods permit one to use conductivity to measure only the component of the sample that is of interest. Further, the sensitivity with which the component of interest is able to be detected is vastly enhanced. Typically, the sensitivity of detection is enhanced by about at least twenty (20) fold over that of an unconcentrated control. The high sensitivity of the present apparatus and methods provides detection of the component in amounts as small as 10 parts per trillion.

SUMMARY

For purposes of illustrative example only and not intended as a limitation of the present apparatus, the apparatus is described herein using an aqueous sample. The apparatus may be adapted for the detection of a selected gas in any vaporizable sample with the proper selection of materials, operating temperatures, and detection means. Also for purposes of illustrative example only and not intended as a limitation of the present apparatus, the apparatus is described herein using carbon dioxide (CO2) as the selected gas to be detected. The apparatus and methods may be adapted for the detection of any selected gas which is soluble and ionizes in a vaporizable sample.

Among the advantages of the apparatus and methods are (1) expendable gases are not required; and (2) reagents are not required either to react or to detect the selected gas.

A liquid sample, such as a relatively large volume of water, is heated to release the dissolved gas in the sample. These gases typically include CO2, oxygen and nitrogen. A portion of the water is evaporated to form a vapor. Sources of ionic interference, such as dissolved salts and metals in the water, remain in the water and do not enter the gas phase along with the vapor. The vapor is, therefore, free of sources of ionic interference.

The vapor is condensed to form a liquid condensate in the presence of the released gases. Equilibrium solubility favors the reabsorption of substantially all of the CO2 released from the heated water into the liquid condensate. Gases, such as oxygen and nitrogen, are not reabsorbed by the condensate due to limited solubility and remain free gases. The free gases may be removed by, for example, a gas permeable, liquid impermeable membrane.

The volume of the liquid condensate is very small compared to the beginning volume of the water sample. The CO2 is, therefore, greatly concentrated in the small volume of the condensate. The condensate is also free of sources of ionic interference.

Detecting the presence and quantifying the amount of CO2 in the condensate may be accomplished by a variety of methods or devices known to those skilled in the art, such as conductivity measurement, optical measurement such as ultraviolet absorption, pH measurement, colorimetric measurement, and others. The preferred mode of detection, however, is direct conductivity measurement.

An apparatus to detect a selected gas in a sample comprising a concentrator that concentrates the selected gas without concentrating sources of ionic interference and a detector in fluid communication with the concentrator is provided. The concentrator comprises a vaporizer to evaporate at least a portion of the liquid sample to form a carrier vapor, a mist trap to remove mist resulting from incomplete vaporization, and a condenser to condense the vapor in the presence of the free selected gas, whereby the selected gas is concentrated in the condensate volume which is free of sources of ionic interference.

To detect a gas in a sample with a sensitivity in the range of parts per trillion, it is important to prevent the carry over of mist when the vapor is condensed. Mist is the result of incomplete vaporization. Mist dropplets, therefore, may contain amounts of dissolved salts or metals that would interfere with the conductivity of the condensate if the mist were carried over to the condenser and contaminated the condensate. That is, mist is undesirable because salts are carried over by the liquid droplets of the mist. Vapor, on the other hand, is desirable because in a vapor all of the liquid is converted to its gas phase and is incapable of carrying over any salts, metals, or other sources of ionic interference. The present apparatus provides a mist trap which corrects for non-ideal operation of the vaporizer and minimizes contamination of the condensate with sources of ionic interference.

Mist may be trapped, for example, by borosilicate glass beads, which provide sufficient surface area and flow characteristics, such as turbulence, so that mist droplets accumulate on the beads and run off as liquid. Liquid from the concentrator may be utilized as a blank control to calibrate the apparatus. For example, a sample flow rate of 5 ml/min may be concentrated to a concentrated analyte flow rate of 0.25 ml/min. 4.75 ml/min of the original sample water volume (from which the dissolved gases have already been released by heat) remains as effluent or run off liquid. A portion of this effluent may be concentrated identically to the analyte sample to serve as a blank. 0.25 ml/min of the effluent liquid may be utilized as a blank, and the remaining 4.5 ml/min of effluent liquid is simply drained from the apparatus.

The amount of the selected gas in the condensed blank is very low, if not virtually undetectable, because the gas was released from the liquid by heating prior to concentration of the blank sample. Such a blank control is very reliable because it is provided from the same sample liquid as the analytical sample.

The apparatus may be adapted to provide such a blank control in parallel with the analytical sample by providing a concentrator comprising a u-tube whereby the analytical sample and the blank control sample are segregated and then concentrated and detected in parallel.

The apparatus performs optimally when the concentrator is tilted from the horizontal so that liquid runs off and is separated from vapor.

METHODS OF $CO_2$ DETECTION

A sample that has been concentrated and vaporized as described herein is now in condition for measurement of the selected component of interest, such as carbon dioxide. The method of measuring or detecting the component of interest may be any suitable method desired.

For example, $CO_2$ may be detected and measured by observing changes in conductivity of a conductive material brought about by the presence of carbon dioxide. Many such methods are possible, and the most prominent of these methods known are summarized below, merely for the purpose of illustrative example and not to limit the scope of the present disclosure and claims.

U.S. Pat. No. 4,666,860, "Instrument for Measurement of the Organic Carbon Content of Water" (reference 1); and U.S. Pat. No. 5,132,094, "Method and Apparatus for the Determination of Dissolved Carbon in Water" (reference 2), are incorporated by reference in there entirety.

Organic contamination of water can be detected by oxidizing the organic material and measuring the conductivity of the $CO_2$ thereby produced. Conductivity may be used since the $CO_2$ gas is in equilibrium with conductive carbonate ions. Various measurement methods are available, as disclosed below. Performance of these methods is compared and described below.

Method 1 includes direct measurement of the sample after oxidation (direct conductivity measurement).

SAMPLE -----> REACTOR ----> SENSOR -----> DRAIN

Since there is no provision for measuring the background, this method is only practical where the conductivity signal of the background, which includes other conductive species in the sample, is negligible compared to the signal from the sample. This method has extremely high error unless used in salt-free and pH-neutral samples, which would-be a rare application.

Method 2 (described in Reference 1) analyzes a discrete sample, permitting measurement of the background prior to oxidation.

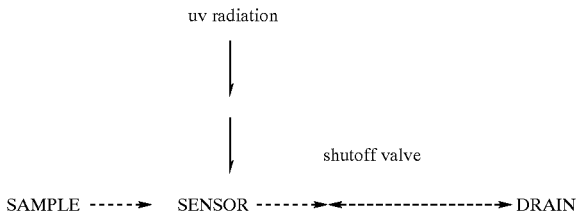

While reducing pH and salt-induced errors, this method is susceptible to error when ionic organic species are present in the sample (i.e., conductivity of acetic acid is greater than the $CO_2$ produced by its oxidation, causing false-negative signals), or in the reaction products (i.e., chlorides in the oxidation of chloroform cause false-positives).

Method 3 uses before and after oxidation by two conductivity sensors to permit continuous on-line monitoring.

SAMPLE ----> SENSOR 1 ----> REACTOR ----> SENSOR 2 ----. DRAIN

In addition to the limitations of Method 2, error is introduced by subtracting signals from two separate sensors.

Method 4 (described in Reference 2) transfers the $CO_2$ across a gas-permeable membrane prior to conductivity measurement.

SAMPLE ----> REACTOR ----> MEMBRANE/DEIONIZED WATER/SENSOR ---->DRAIN

Thus, ionic interference is eliminated, except for those compounds having both ionic and gas phases in water (i.e., iodine).

Method 5, the current apparatus, concentrates the sample to provide high signal-to-noise. The CO2 concentration is increased, thereby providing a sensitivity gain which may be greater than twenty (20) times the sensitivity of methods 1–4, above.

$CO_2$ is removed from the sample by boiling, and then is recovered, highly concentrated, in a small volume of condensate. Increased sensitivity is obtained by increasing sample volume and/or decreasing condensate volume. Ionic interference is retained in the spent sample leaving the concentrator.

A detector suitable for the present apparatus comprises a conductivity cell comprising:
sample inlet;
an annular flow electrode in fluid communication with the inlet; and
a display connected to the annular flow electrode,
whereby the display shows changes in the conductivity of the electrodes in the presence of a selected gas.
The conductivity cell may comprise concentric tubular electrodes.

The present apparatus and methods may be adapted for either continuous process monitoring or for batch mode analysis.

DETAILED DESCRIPTION

Figure 1A:
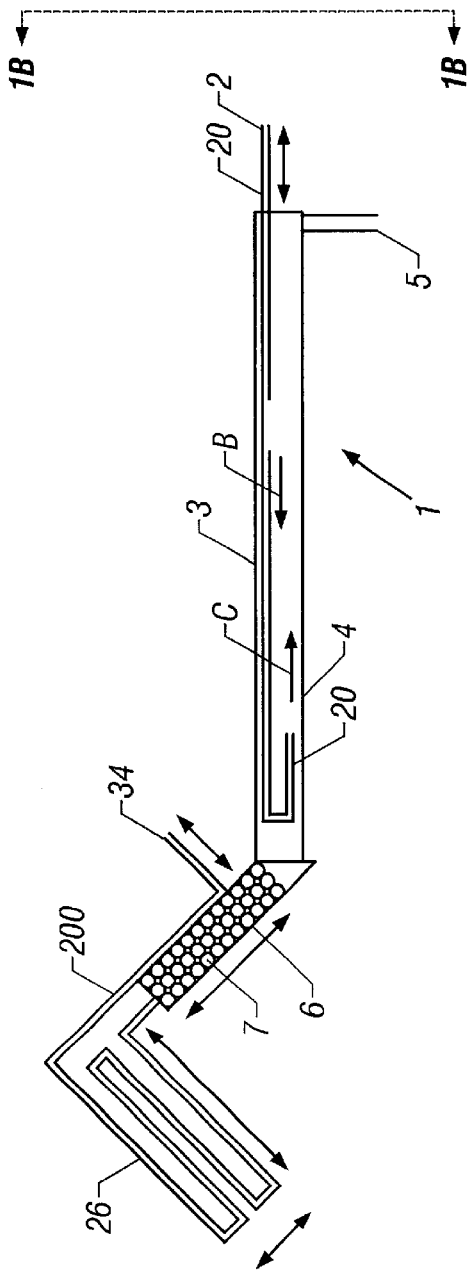
FIGS. 1a,1b is a cross-sectional, schematic view of one embodiment of a gas concentrator.
Figure 1B:
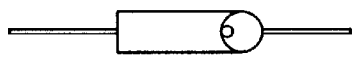

Refer to FIG. 1, showing a cross-section of the $CO_2$ concentrator, designated generally by numeral 1. The water sample enters injector 20 through inlet 2 where the sample's temperature is raised to release dissolved gases. The sample is then introduced into vaporizer 3 to evaporate at least a portion of the water to form a vapor. Vaporization occurs along lower vaporizer tube wall 4.

Liquid injector 20 is flush with and parallel to lower vaporizor 3 wall 4. The direction of vapor flow is shown by arrow b. The direction of liquid flow is shown by arrow c.

Mist trap 6 removes mist from the vapor to remove substantially all sources of ionic interference that would otherwise be carried over to condenser 26 and contaminate the condensate.

Liquid flows downward by gravity in a thin film along wall 4, minimizing splashing and mist formation in the upward vapor flow, thereby avoiding ionic carryover. Vaporizer 3 is slightly tilted so that gravity induced liquid flow provides sufficient residence time for conversion of all CO2 species in the liquid condensate to the gas phase. The amount of tilting is empirically determined for a particular situation, but experience indicates that a tilt of about 15 to 45 degrees from the horizontal usually provides sufficient residence time. Spent liquid is drained form the bottom of vaporizer 3 at sample drainage port 5.

Vapor flow rises to mist trap 6 which corrects for non-ideal operation of the vaporizer stage. Mist trap 6 has three important tasks: 1) it traps and returns any mist to vaporizer 3; 2) it equilibrates the temperature of any overheated steam to the boiling point; and 3) it prevents vaporizer water from flowing into the condenser as a steam-swept surface film (surface entrainment). Flow through glass beads 7 creates turbulence causing filtering of small mist particles by impingement on the large, wet, hydrophilic surface of beads 7 so that mist particles grow into a small net flow of liquid back toward vaporizer 3.

Upon condensation in condenser 26, CO2 reabsorbs into the liquid water condensate, which has a relatively small volume, and is concentrated free of ionic interference. The temperature is lowered to a minimum in order to maximize the dissolved CO2, i.e., the ionic species that is to be detected.

The condensate flows through outport 34 to be detected by a conductivity cell (FIG. 2) in fluid communication with port 34.

Low conductivity detection limits require a chemically-resistant material for the apparatus, including the mist trap beads. Borosilicate glass was selected for several reasons: 1) it possesses excellent wetting characteristics and non-porous surface, which facilitate the maintenance of thin films of water; 2) it is easy and inexpensive to fabricate; 3) it is convenient for visual inspection; and 4) it is not attacked aggressively by pure water.

Figure 2:
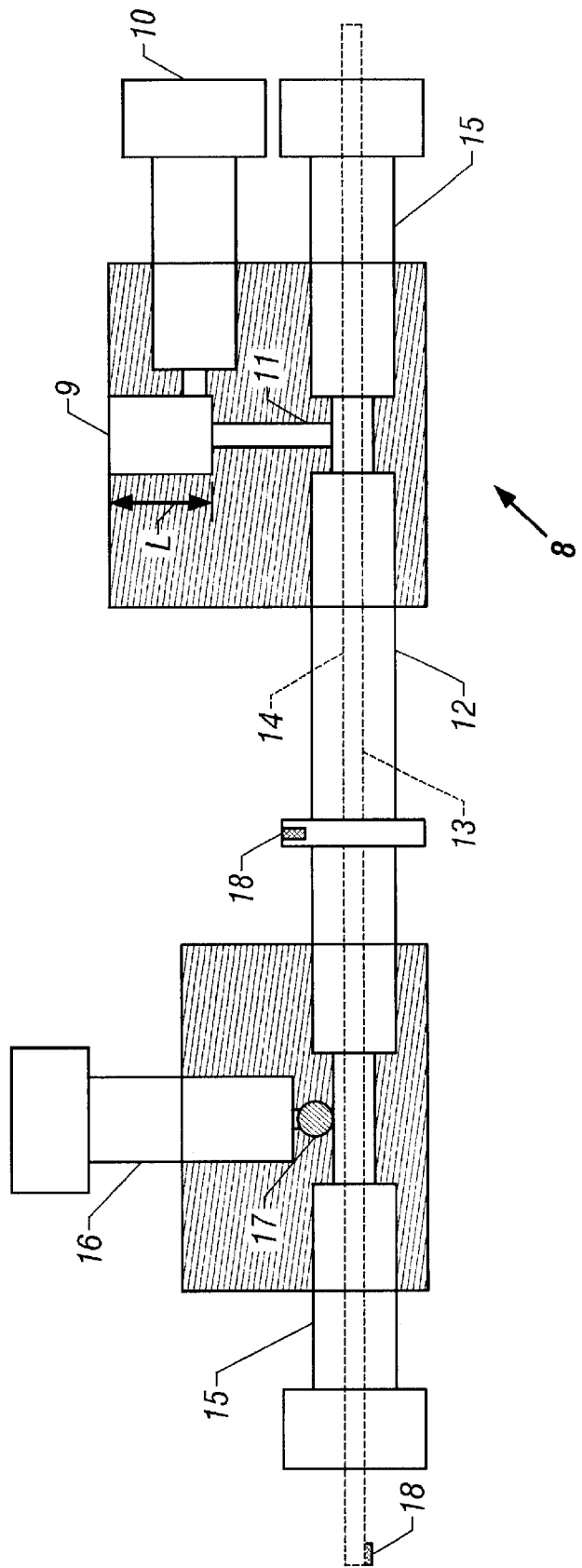
FIG. 2 is a cross-sectional view of an annular-flow conductivity cell.

Refer now to FIG. 2, which is a cross-sectional schematic diagram of an annular-flow conductivity cell for $CO_2$ detection, designated herein generally by the numeral 8, of the apparatus. The sample, concentrated in concentrator 1 (FIG. 1) is preconditioned before conductivity measurement in cell 8. Free gases are removed through a hydrophobic membrane across port 10. The sample enters conductivity cell 8 through inlet port 10 into mixing chamber 9 and through passage 11 to annular-flow cell 12. Port 10 is in fluid communication with, or identical to, port 34 of FIG. 1.

Conductivity is measured in annular-flow cell 12, which comprises concentric tubular electrodes: inner electrode 13 and outer electrode 14. Electrodes 13,14 respond to the presence of CO2 with a change in conductivity. Electrodes 13, 14 are retained in cell 8 by electrode retainers 15. This configuration minimizes both the cell constant, for maximum sensitivity, and the sample volume while achieving plug flow.

Conductivity cell 8 also comprises fluid outlet port 16. A Temperature Sensor 17 is located between electrodes 13, 14, and port 16. Mechanical/electrical connection 18 may be connected to a suitable conductivity indicator display such as a needle and gauge or a digital readout.

Figure 3:
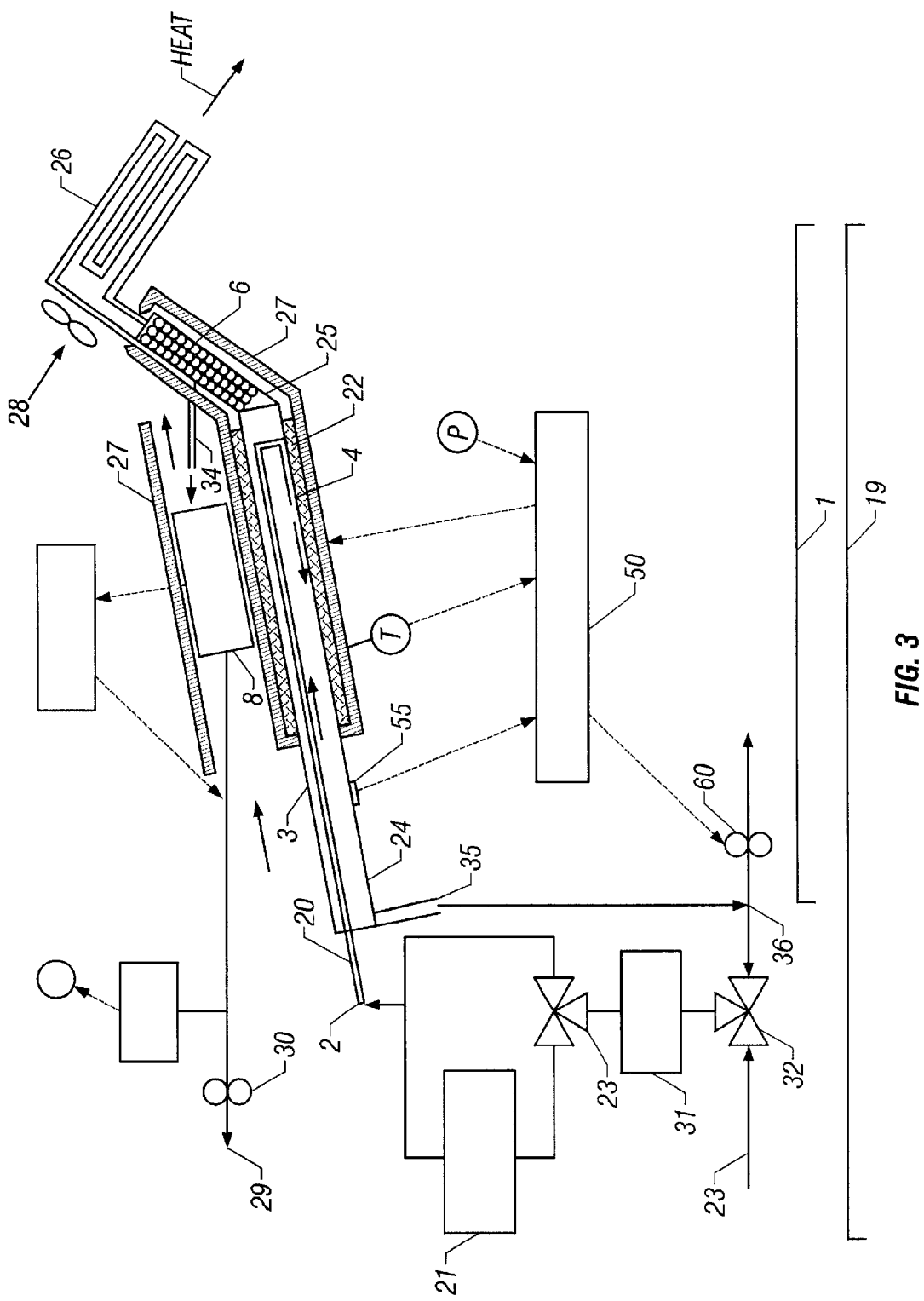
FIG. 3 is a cross-sectional, schematic view of one embodiment of a gas analyzer apparatus.

FIG. 3 is a cross-sectional, schematic diagram of a gas analyzer apparatus, generally designated herein by the numeral 19. CO2 Concentrator 1 and Annular-Flow Conductivity Cell 8 are incorporated into TC/TIC analyzer 19 for continuous process monitoring applications.

CO2 Concentrator 1 comprises an all borosilicate glass unitized assembly mounted in insulated metal heater block 22. Inlet 23 is in fluid communication with reactor 21. Condensate-out port 34 is in fluid communication with Conductivity Analyzer 8. Drain 35 conduits fluid to drain tee 36.

A sample enters reactor 21 through inlet 20, shown in FIG. 3 as a T valve, to convert organic carbon to CO2. The reacted sample enters vaporizer 3 through inlet 2. The sample first encounters sample preheater tube 20, comprising, for example, a cylindrical tube of ⅛ inch ID and 17 inches long. Sample injector/preheater tube 20 provides sensible heat to raise the temperature of the sample to its boiling point.

Injector 20 transports the preheated sample into vaporizer tube 24, comprising, for example, a cylindrical tube approximately 15 inches long and having a 0.5 ID. In the example illustrated here, injector/preheater tube 20 extends substantially into vaporizer tube 24, which is easily accomplished because vaporizer tube 24 has an internal diameter greater than the outer diameter of injector 20. CO2 and free gases are carried in tube 24 by the flow of steam.

For optimal performance, vaporizor 3 is tilted from the horizontal to direct liquid flow downward tangentially along tilted tube wall 4 to minimize splashing (which can cause mist pickup in the upward vapor flow), thereby preventing ionic carryover.

Heater block 22 may be mounted around vaporizer tube to provide heat to vaporizer tube 24. Heater block 22 also insulates tube 24 from losing heat.

Temperature (T) and pressure (P) monitors or controls, 50 may also be installed to control or monitor the temperature and pressure in tube 24. This example also shows tube 20 being bent in roughly a U-shape to gently direct liquid flow downward along vaporizer wall 4 without splashing.

The vaporized sample enters mist trap 6, comprising, for example, cylindrical tube 25, approximately 3 inches long and having about a one-half inch ID, filled with 3 mm glass beads or balls to prevent liquid carryover to condenser 26.

Insulation 27 may be wrapped around vaporizor tube 24, mist trap 6 and heater block 22 to substantially prevent the loss of heat from the these elements of the apparatus.

Condenser 26, in fluid communication with mist trap 6, condenses vapor from vaporizer 3. In the preferred embodiment, condenser 26 comprises a peltier condenser, comprising stainless steel tubing and further comprising airfoil fins to increase the surface area for better cooling. Interfacing fan 28 transfers latent heat away from condenser 26.

The now concentrated sample flows from condenser 26 to conductivity analyzer 8. Conductivity analyzer 8 may comprise a conductivity meter, for example the MONEC D 9135 modified for parts per trillion carbon (pptc) computing and display. An algorithm is used for converting uS/cm to pptC and an algorithm for faster response by first-order exponential may be used.

Analyzer 8 also comprises insulated housing 28, drain 29, pump 30 controls condensate flow to facilitate drainage out of drain 29. A temperature control algorithm that uses a sensor in analyzer 8 for feedback may also be used to maintain a constant, elevated temperature to analyzer 8. Regardless of whether a temperature control algorithm is used or not, it is important to measure the temperature of the sample in analyzer 8 to calculate the $CO_2$ level in the sample.

We now turn for a closer look at the management of condensation disclosed above by means of vaporizer 3, mist trap 6, and condenser 26. Recall that vaporizer 3 comprises preheater tube 20, vaporizer tube 24, heater block 22. Vaporizer 3 is tilted with respect to the horizontal, and mist trap 3, in fluid communication with vaporizer 3, is tilted upward in relation to vaporizer 3. These elements cooperate to provide condensate flow control to control the rate of vapor production. Vapor production is controlled by managing the dynamic equilibrium state between the gaseous vapor state and the liquid condensate state of the sample. This equilibrium can be managed by regulating the temperature and pressure of the system and regulating the flow of liquid runoff.

Temperature is regulated by insulated heater block 22 comprising a heater of sufficient power to at least partially vaporize the sample, for example, to heat a liquid sample to or above its boiling point. 125 watts has been found suitable for water, but is disclosed merely for illustrative purposes and not to limit the scope of the claims appended hereto.

Pressure/temperature transducer 50 may be connected to vaporizer 3 to provide pressure regulation in vaporizer 3 to achieve and maintain a desired liquid level in vaporizer 3. 0–15 pounds per square inch (psig) has been found, empirically, to be suitable for proper instrument operation. Peristaltic pump 60 connected to vaporizer 3, either indirectly through pressure transducer 50, or independently of pressure transducer 50, provides pressure which is measured by pressure transducer 50. Heat and pressure are supplied to the system to achieve or maintain the desired production rate. The state of the liquid/vapor equilibrium may be determined by measuring the flow rate of the liquid condensate. The condensate flow rate may be regulated by peristaltic pump 30. A pump capable of approximately 0.2 to 0.5 cc/min has been found suitable for ppt sensitivity.

Temperature and pressure can be regulated in vaporizer 3 simply by providing an over-pressure release mechanism, such as a pressure actuated valve, and providing an over-temperature shut off mechanism, such as a thermostat, whereby the heat input into the vaporizer is at least sufficient to assure vaporization of the sample.

A controlled condensate flow rate of approximately 0.2 to 0.5 cc/min has been found suitable for parts per trillion sensitivity. In its best mode, condensate flow control further comprises a pressure/temperature control algorithm to control the system automatically and/or by computer and a condenser cooling fan to cool condenser 26 by removing sensible and latent heat from water vapor.

Reactor 21 is provided for converting organic carbon to $CO_2$ prior to CO2 concentration, if desired. Reactor 21 may be modified or adapted, as necessary, for fluid connection to a CO2 concentrator such a shown in FIG. 1. A reactor such as described in U.S. Pat. No. 5,413,763 has been found suitable for ppt sensitivity.

The preferred embodiment also comprises, connected to the apparatus, sample pump 31, such as an FMI pump or a constant pressure orifice or other suitable means, to facilitate introduction of the sample into the apparatus (a flow rate in the range of 2 to 10 ml/min has been found, empirically, to be suitable for sample introduction); sample select valve 32; and Total Carbon/Total Inorganic Carbon (TC/TIC) mode select valve 23, such as a 3-way valve.

A blank—water without $CO_2$—is generated from the effluent of the sample leaving concentrator 1. The liquid effluent from the sample is pure water, containing no $CO_2$, since all the $CO_2$ was released from the sample and concentrated in the vapor. A portion of the effluent water may be concentrated as a blank control, and CO2 detected in the blank control.

Condenser 26 is preferably of stainless steel, which has better heat transfer properties than glass. Fan 28 is used to remove heat for condensation. Condenser 26 is partitioned to keep the sample and the blank segregated. Condensation is enhanced by fan 61.

Figure 4A:
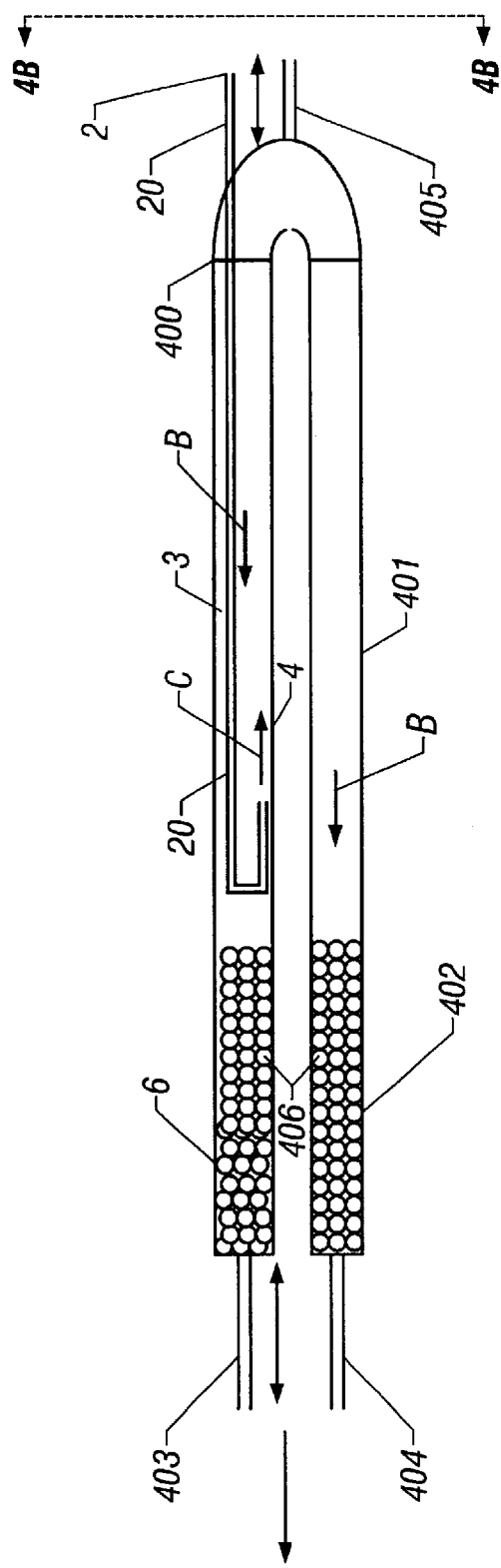
FIG. 4a is a cross-sectional, schematic, side view of an alternative embodiment of a gas concentrator suitable for parallel analysis of an analytcal sample and a blank control sample.
Figure 4B:
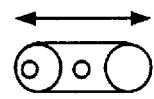
FIG. 4b is a cross-sectional, front schematic view of a gas concentrator of FIG. 4a. along line A—A.

FIG. 4a is a cross-section schematic drawing of another concentrator of the apparatus suitable for parallel analysis of an analytical sample and a blank control sample. The FIG. 4b is front schematic view of the concentrator of FIG. 6a along line A—A.

U-tube 400 provides an instrument blank. A sample enters the concentrator at port 2 through liquid injector 20 where dissolved gases are released from the liquid by heat. At least a portion of the liquid is vaporized. Liquid from incomplete vaporization and mist trap run off flow in the direction of arrow c along wall 4, around the turn of u-tube 400 to blank vaporizer 401, where the liquid is vaporized. Mist trap 402 removes mist from incomplete vaporization. Beads 406 in mist traps 6, 402, may be dimpled to enhance the capture of mist droplets by increasing the surface area of beads 406 and by increasing the turbulence of the vapor flow. Blank vapor is conducted through port 404 to a condenser. Excess fluid is expelled through drain port 405. Analyte vapor passes through analyte mist trap 6, through port 403 to a condenser.

Figure 5:
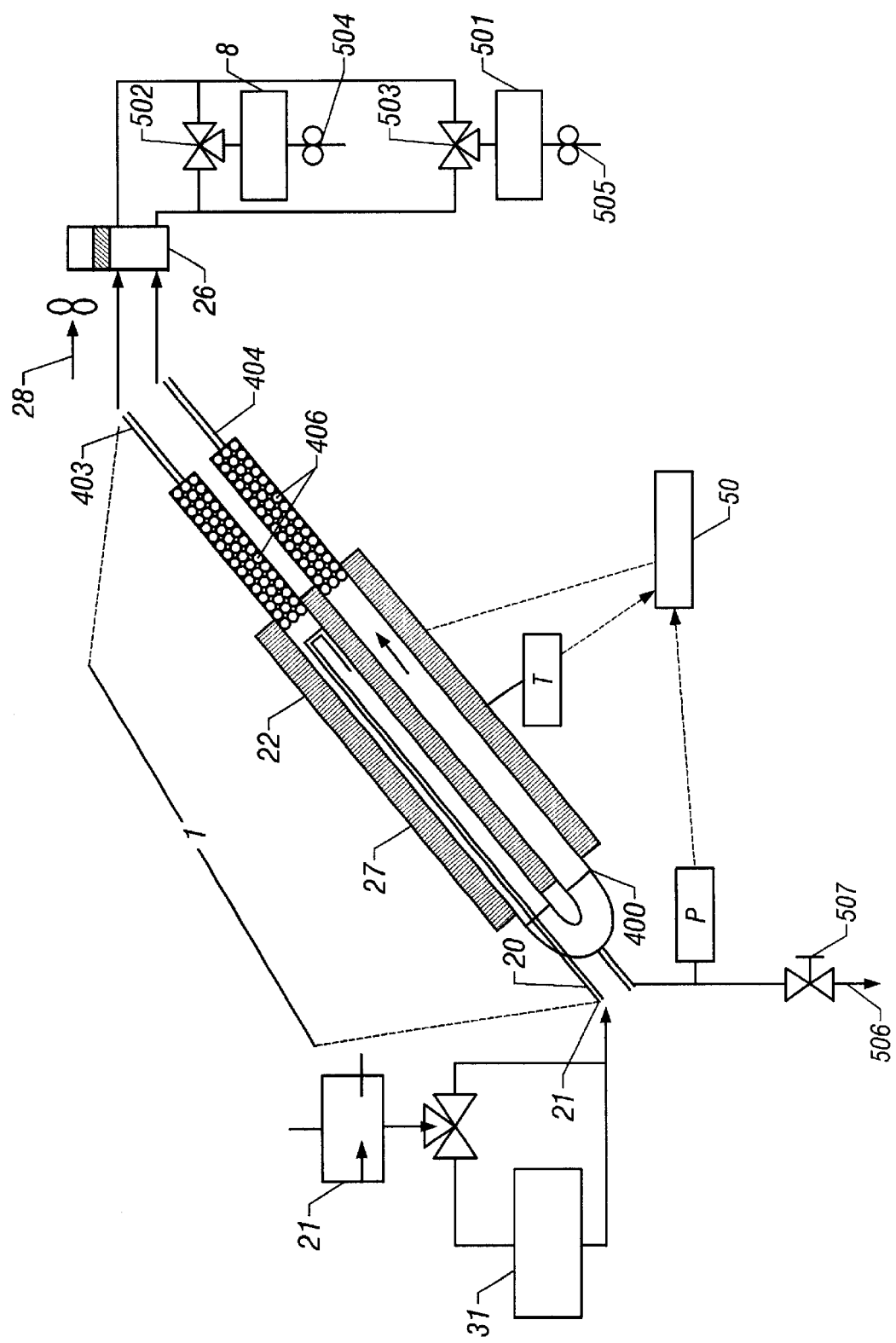
FIG. 5 is a cross-sectional, side schematic view of another embodiment of a gas analyzer apparatus comprising the concentrator of FIG. 4a,b.

FIG. 5 is a cross sectional schematic of another embodiment of a gas analyzer apparatus comprising the concentrator of FIG. 4a,b. This apparatus is substantially similar to that of FIG. 3, with corresponding elements sharing the same numeral designation. Further provided, however, is u-tube concentrator 400. Also provided is a second detector in fluid communication with condenser 26 for detection of a selected gas in the blank sample.

The Blank provides a baseline reference used to correct for any non-ideal performance induced by the environment of the instrument. Both analytical and blank signals are continuously monitored to provide a net signal for $CO_2$ concentration computing and reporting.

The liquid level in vaporizer 3 is controlled by maintaining its temperature and pressure (i.e., there is no liquid level sensor in this embodiment).

The temperature of the conductivity cells is not actively controlled for two reasons:
  1. $CO_2$ is less soluble at higher temperature, which could adversely affect recovery;
  2. active temperature control induces noise.

Condenser 26 may be a peltier condenser. Unabsorbed gases such as nitrogen and oxygen are expelled through gas permeable, liquid impermeable membranes across ports 502, 503 while condensate passes through to conductivity cell 8,501.

Cells 8,501 are periodically calibrated to ensure they read identical values for the same sample. Spent condensate is expelled from each cell 8, 501 by ports 504, 505 respectively.

Also shown is drain 506, and back pressure regulator 507.

The amount of $CO_2$ in the sample is determined by comparing the conductivity of the sample with the conductivity of the blank.

Although exemplary embodiments of the apparatus and methods have been shown and described, many changes, modifications, and substitutions may be made by one of ordinary skill in the art without departing from the spirit and scope of this invention.

What is claimed is:

1. An apparatus for detecting a selected gas in a liquid sample, the apparatus comprising;
    a concentrator to concentrate the selected gas in the sample without concentrating sources of ionic interference, comprising:
        a vaporizer to expel the selected gas out of the liquid sample and to evaporate at least a portion of the liquid sample to form vapor;
        a mist trap in fluid communication with the vaporizer to capture mist droplets from the vaporizer; and,
        a condenser in fluid communication with the mist trap to condense the vapor to a liquid condensate, whereby the selected gas in the vapor is sorbed and concentrated in the liquid condensate; and,
    a detector in fluid communication with the concentrator to detect the selected gas in the sample.

2. The apparatus of claim 1, wherein the concentrator is tilted from the horizontal.

3. The apparatus of claim 1, further comprising a reactor in fluid communication with the concentrator to react the sample prior to concentration.

4. The apparatus of claim 1, where in the apparatus is adapted for continuous process monitoring applications.

5. The apparatus of claim 1, wherein the apparatus operates in batch mode.

6. The apparatus of claim 1, wherein the apparatus is adapted for total carbon/total inorganic carbon analysis of a sample.

7. The apparatus of claim 1, further comprising a hydrophobic membrane attached to the concentrator to remove unabsorbed gases from the apparatus.

8. The apparatus of claim 1, wherein the detector comprises concentric tubular electrodes.

9. The apparatus of claim 1, wherein the detector detects changes in conductivity in the presence of the selected gas.

10. The apparatus of claim 1, wherein the selected gas comprises carbon dioxide.

11. The apparatus of claim 1, wherein the liquid comprises water.

12. The apparatus of claim 1, wherein the concentrator comprises inert material where the sample comes into contact with the concentrator.

13. The apparatus of claim 12, wherein the inert material comprises borosilicate glass.

14. The apparatus of claim 1, wherein the mist trap comprises inert beads.

15. The apparatus of claim 14, wherein the beads comprise borosilicate glass.

16. The apparatus of claim 1, wherein the concentrator comprises a u-tube to separate the analytical sample from a blank.

17. The apparatus of claim 1, wherein the selected gas is detected in amounts as small as 10 parts per trillion.

18. A method for detecting a selected gas in a liquid sample, the method comprising:
    providing a concentrator to concentrate the selected gas in the sample without concentrating sources of ionic interference;
        the concentrator comprising:
            a vaporizer to expel the selected gas out of the liquid sample and to evaporate at least a portion of the liquid sample to form vapor;
            a mist trap in fluid communication with the vaporizer to capture mist droplets from the vaporizer; and,
            a condenser in fluid communication with the mist trap to condense the vapor to a liquid condensate, whereby the selected gas in the vapor is sorbed and concentrated in the liquid condensate;
        providing a detector in fluid communication with the concentrator to detect the selected gas in the sample;
        introducing the sample into the concentrator;
        concentrating the selected gas without concentrating sources of ionic interference; and
        detecting the concentrated selected gas.

19. The method claim 18, further comprising reacting the sample to produce the selected gas prior to concentrating the gas.

20. The method of claim 18, wherein the method is adapted for continuous process monitoring applications.

21. The method of claim 18, wherein the method is adapted for batch mode analysis.

22. The method of claim 18, wherein the method is adapted for total carbon/total inorganic carbon analysis of a sample.

23. The method of claim 18, wherein the method is reagentless.

24. The method of claim 18, wherein the selected gas is detected in amounts as small as 10 parts per trillion.

25. A method for high sensitivity detection of CO2 in liquid water, the method comprising:
    heating the liquid water to release CO2 from the heated liquid water;
    evaporating at least a portion of the heated liquid water to form a vapor;
    condensing the vapor to form a liquid condensate, whereby CO2 is absorbed and concentrated in the liquid condensate; and
    detecting the amount of CO2 in the liquid condensate.

26. The method of claim 25, further comprising a removing any unabsorbed gases after the unabsorbed gases are released from the liquid water.

27. The method of claim 25, further comprising:
    detecting the amount of CO2 in the liquid water after the CO2 has been released from the liquid water by heat to provide a baseline blank measurements.

28. The method of claim 25, wherein the method is reagentless.

29. The method of claim 25, wherein the CO2 is detected in amounts as small as 10 parts per trillion.

* * * * *